(12) United States Patent
Novak (10) Patent No.: US 12,163,178 B2
(45) Date of Patent: Dec. 10, 2024

(54) DEVICE FOR RANDOM BLOOD SUGAR TESTING AND THE METHOD OF ITS USE

(71) Applicant: XGLU LABS A. S., Ceske Velenice (CZ)

(72) Inventor: Marek Novak, Ceske Velenice (CZ)

(73) Assignee: XGLU LABS A. S., Ceske Velenice (CZ)

( * ) Notice: Subject to any disclaimer, the term of this patent is extended or adjusted under 35 U.S.C. 154(b) by 370 days.

(21) Appl. No.: 17/284,856

(22) PCT Filed: Oct. 2, 2019

(86) PCT No.: PCT/CZ2019/050042
§ 371 (c)(1),
(2) Date: Apr. 13, 2021

(87) PCT Pub. No.: WO2020/207514
PCT Pub. Date: Oct. 15, 2020

(65) Prior Publication Data
US 2022/0017936 A1    Jan. 20, 2022

(30) Foreign Application Priority Data
Apr. 11, 2019   (CZ) ................................ CZ2019-228

(51) Int. Cl.
*C12Q 1/00*       (2006.01)
*G01N 27/327*   (2006.01)

(52) U.S. Cl.
CPC ......... *C12Q 1/006* (2013.01); *G01N 27/3272* (2013.01); *G01N 27/3277* (2013.01)

(58) Field of Classification Search
CPC ............... C12Q 1/006; G01N 27/3272; G01N 27/3277; G01N 33/4875; G01N 27/3273;
(Continued)

(56) References Cited

U.S. PATENT DOCUMENTS

2001/0046569 A1* 11/2001 Yoneya ............. G02F 1/133711
428/1.23
2004/0138543 A1   7/2004 Russel et al.
(Continued)

FOREIGN PATENT DOCUMENTS

WO       2006085258 A2    8/2006

*Primary Examiner* — Jill A Warden
*Assistant Examiner* — John McGuirk
(74) *Attorney, Agent, or Firm* — Rivka Friedman (57) ABSTRACT

The device is composed of at least one disposable biosensor (2) for applying a blood sample, as well as evaluation electronics (1) for retrieving and processing information from the disposable biosensor (2) with the applied blood sample, as well as a display (7) for displaying information from the evaluation electronics (1). Disposable biosensors (2) and a display (7) are arranged in a common vapour non-permeable closable space, wherein the display (7) is hygroscopic to bind air moisture which would otherwise be bound by disposable biosensors (2). The display (7), evaluation electronics (1) and disposable biosensors (2) can be arranged on a common support substrate (4), wherein the support substrate (4) is provided with a removable and/or openable vapour non-permeable container. Disposable biosensors (2) can be detachable from the support substrate (4).

8 Claims, 4 Drawing Sheets

(58) Field of Classification Search
CPC .. G01N 33/48778; G01N 27/02; G01N 33/66; G01N 2021/0106; G01N 2021/5938; G01N 33/006; G01N 33/0063; G01N 2035/00891; A61B 5/14532; A61B 5/1486; A61B 5/145; A61B 5/1455; A61B 5/1468; A61B 5/742; A61B 6/461; C09K 19/02; C09K 19/04
USPC .......................................... 340/182; 422/403
See application file for complete search history.

(56) References Cited

U.S. PATENT DOCUMENTS

| | | | |
|---|---|---|---|
| 2006/0121624 A1 | 6/2006 | Clemens et al. | |
| 2009/0178937 A1* | 7/2009 | Taylor ................ | G01N 27/3273 205/792 |
| 2014/0312054 A1* | 10/2014 | Crawford .......... | B65D 83/0829 221/232 |
| 2018/0085041 A1 | 3/2018 | Leichner | |

* cited by examiner

DEVICE FOR RANDOM BLOOD SUGAR TESTING AND THE METHOD OF ITS USE

FIELD OF THE INVENTION

The invention relates to the field of in-vitro diagnostic disposable devices for blood sugar testing by means of a blood drop sample, especially in diabetics.

BACKGROUND OF THE INVENTION

The device for testing the concentration of glucose present in the blood, i.e. blood sugar level, is generally called "glucose meter". Glucose meters are particularly designed for diabetics or people with impaired blood sugar management, whether due to diabetes or other medical causes. Blood sugar testing is generally performed by means of a disposable biosensor on which a sample of a user's capillary blood drop is applied. A drop of blood is most often obtained from the user's fingers. A disposable biosensor can be integrated in a disposable test strip that will be inserted, after application of the blood sample, into a device containing evaluation electronics for testing and a display for displaying evaluated information from testing, which are placed in a plastic body forming a device case. The display is usually an LCD or OLED display, and must be able to show at least the value of blood glucose concentration. The device is provided with a suitable power source, e.g. a battery or a photovoltaic strip.

The innovation in the field of blood sugar testing includes continuous sensors for blood sugar testing that are capable of testing tens to hundreds of values per day at intervals of several minutes. These types of sensors are especially suitable for type I diabetics with an intensified insulin regimen. For other patients, whose therapeutic regimen is characterized by less frequent testing (several times a week to twice a day), the use of standard glucose meters and continuous glucose meters is not particularly suitable both in terms of the comfort of a patient who must carry and keep a relatively large electronic device, and in terms of the cost of device.

In some cases, it is necessary to have a device for blood sugar testing that allows random, in other words irregular, testing such as in one-day screening when a user suspected of having problems with blood sugar performs regular tests for a period of one day on the selected day of the week or month in order to detect any hidden health problems. At the same time, there are problems with the protection of disposable biosensors for glucose meters with irregular use from air moisture, especially after unpacking a factory container and using once in a while just a fraction of contained disposable sensors stored in an open factory container. Now, this is most often solved by adding a desiccant either in the body of the container with disposable testing biosensors or in the form of a bag with desiccant properties, wherein both solutions adversely affect the production costs, compactness, and last but not least the amount of produced waste material. Occasional users are not interested in investing resources in glucose meters that are specialized for regular testing in an intensive regimen and, at the same time, in glucose meters that have a separate electronic evaluation unit and an external container with disposable biosensors provided with a desiccant because they can reduce user's comfort due to obligation to keep them concurrently.

The above problem is solved by the invention of US 2004/0138543 A1, which presents a device consisting of a single box, inside which both disposable biosensors and evaluation electronics are arranged. Disadvantages of the device consist in the fact that the used disposable biosensors are returned inside the device, which reduces hygienic cleanliness and, moreover, disposable biosensors are not protected from binding air moisture, leading to their degradation over time.

The above problem related to hygiene and the protection from air moisture is solved by the invention of US 2018/085041 A1, which presents disposable biosensors in the box provided with the sorbents for absorption of moisture and other contaminants. After use of the invention, it is possible to dispose of the used biosensor, wherein the prolonged irregular use from unpacking the factory container has no effect on the degradation of biosensors thanks to sorbents absorbing air moisture. Disadvantages of the invention are that the biosensors are provided with cases with a desiccant, which increases the costs of producing the device of the invention and imposes some burden on the environment due to excess waste material.

The present invention is to provide a device for random blood sugar testing, which would preserve the quality of disposable biosensors long after unpacking the factory container, in particular by protecting them from air moisture intermittently re-entered inside the container in each use of part of the disposable biosensors placed in the container, which would use only minimum necessary components to make it compact and not to disrupt user's comfort and, due to its disposable character, to impose burden on the environment to the necessary extent and, at the same time, which would have low acquisition costs due to its disposable character.

SUMMARY OF THE INVENTION

The task is solved by developing a device for random blood sugar testing according to the following invention.

The device for random blood sugar testing is composed of at least one disposable biosensor for applying the blood sample. Furthermore, the device of the invention consists of evaluation electronics for retrieving and processing information from a disposable biosensor with the blood sample applied. And last but not least, the device of the invention includes a display to show information with the test result sent from the evaluation electronics.

The summary of the invention rests in the fact that the disposable biosensors and the display are arranged in a common vapour non-permeable closable space, wherein the display is hygroscopic.

An advantage of the invention is that the display that is an integral part of the device will assume the role of the desiccant, which has the task to protect the disposable biosensors from air moisture in infrequent taking of disposable biosensors for random tests. The absence of a separate desiccant reduces the requirements for the size of the device and its containers, reduces the amount of waste produced, while reducing the acquisition costs of the device.

In a preferred embodiment of the device of the invention, the display, evaluation electronics and disposable biosensors are arranged on a common support substrate wherein the support substrate is provided with a removable and/or openable vapour non-permeable container. The advantage of the common support substrate is compactness of the whole device. In addition, design of the present invention solves one of the biggest problems of enzymatic sensors, i.e. their high susceptibility to moisture. Today it is necessary to place the strip in a moisture-controlled environment, in practice usually in a box with a suitable desiccant (e.g. silica gel).

However, for the given type of design, this is extremely disadvantageous; disposable glucose meters designed on a flat surface are optimized for low thickness and addition of another object in the container will adversely affect the compactness. User can easily keep an eye on whether he/she has only one object compared to the background of the invention, when the user must carry an electronic device and a container with disposable biosensors.

In another preferred embodiment of the device of the invention, disposable biosensors are separable from the support substrate. It is preferable because it is possible to break off the used biosensor with fingers from the support substrate and dispose it to ensure that, in terms of hygiene, it does not pose a risk for the remaining unused disposable biosensors and the whole device.

In another preferred embodiment of the device of the invention, the display is the electrochromic, wherein its electrolyte has desiccant properties. The displays used today as standard in consumer electronics and medical devices are mainly the LED, LCD and OLED types. These types of displays are characterized by a relatively high output price, while the display in the device of the invention is realized, in terms of costs, on a production-inexpensive electrochromic principle, which is suitable for disposable devices, which are thrown into the waste after use. Preferably, the salt concentration in the electrochromic display is set so that the electrolyte solution of the electrochromic display at normal room temperature and pressure acts as a desiccant, i.e. vapour pressure of water in ambient air is greater than vapour pressure in the electrolyte. In this case, there will be transfer of water from the environment into the electrolyte of the display. This will transfer moisture from the area of biosensors, where the moisture is undesirable, into the electrolyte of the display, where, on the contrary, the moisture is very desirable.

In another preferred embodiment of the device of the invention, the electrolyte of the electrochromic display contains at least one chemical substance of the group of zinc chloride, calcium chloride, ferric chloride, potassium carbonate, potassium phosphate, potassium nitrate, potassium hydroxide, sodium hydroxide. At the same time, the preferred embodiment is when the electrochromic display contains at least one electrochromic substance of the group of viologen, complex iron compound, PEDOT:PSS, polyaniline, polypyrrole.

It is preferable because most electrochromic displays that are currently used in other fields of technology, are based on the toxic solvents with a high boiling point, or ionic liquids. The high boiling point reduces effectively the vapour pressure of the solvent which is then slower evaporated from the display. The toxicity and the difficulty of finding polymers and adhesives which resist organic solvents, are then the largest negative of known electrochromic displays. The design of the device of the invention is a preferred constructional solution, in which the display of the device with an appropriate composition of the electrolyte and electrochromic substances and the concept represents a function of the desiccant, wherein its production costs are very advantageous for use in the invention herein and, moreover, the impact on the environment in terms of waste management is minimal for the mentioned use in the invention.

In another preferred embodiment of the device of the invention, the display is provided with a vapour permeable cover barrier layer for water-based liquids. The cover barrier layer protects the display from damage, in particular from soaking with liquid water. The display must adopt the air moisture in vapour form but it could not be allowed to suck a larger volume of water in the form of liquid once in order to maintain its function as a protective desiccant.

In another preferred embodiment of the device of the invention, disposable biosensors are provided with at least one enzyme of the group of glucose oxidase, glucose dehydrogenase, peroxidase. These enzymes are useful for amperometric evaluation of glucose level in a blood sample but, at the same time, are very susceptible to bind air moisture. The invention enables their use because it can well protect them from air moisture.

In another preferred embodiment of the device of the invention, the evaluation electronics comprise at least one memory device with stored calibration constants of disposable biosensors. If the calibration constants of biosensors are stored in the memory of the evaluation electronics in the production of the device, there is no obligation to calibrate the evaluation electronics for each biosensor used, thus simplifying the evaluation electronics. In addition, blood sugar testing is accelerated. The memory device may also be used to store calibration constants of frequency oscillator. Today, crystal oscillators are mainly used in electronics, which show great precision; the disadvantage is their price. In fact, a stable oscillator can be created directly on the chip. Its disadvantage, however, is the inaccuracy of output frequency which can be compensated by measuring oscillator frequency in addition to calibration constants for disposable sensors in the production and on the basis thereof, the constants will be calculated and stored in the memory device to ensure that the timing will be precise for all products.

The invention also includes a method of using the above device for random blood sugar testing, whose principle consists in using the invented device in the so-called one-day screening. Using the devices for one-day screening is advantageous because the current state only offers glucose meters for intensive daily blood sugar testing. The invented device perfectly meets the needs of users who carry a small and inexpensive device used once in a while.

The main advantages of the invention include the elimination of a spare inserted desiccant as well as compactness, low production costs, hygiene, suitability for infrequent use and reduced waste load.

EXPLANATION OF DRAWINGS

The present invention will be explained in detail by means of the following figures where.

EXAMPLE OF THE INVENTION EMBODIMENTS

It shall be understood that the specific cases of the invention embodiments described and depicted below are provided for illustration only and do not limit the invention to the examples provided here. Those skilled in the art will find or, based on routine experiment, will be able to provide a greater or lesser number of equivalents to the specific embodiments of the invention which are described here.

Figure 1:
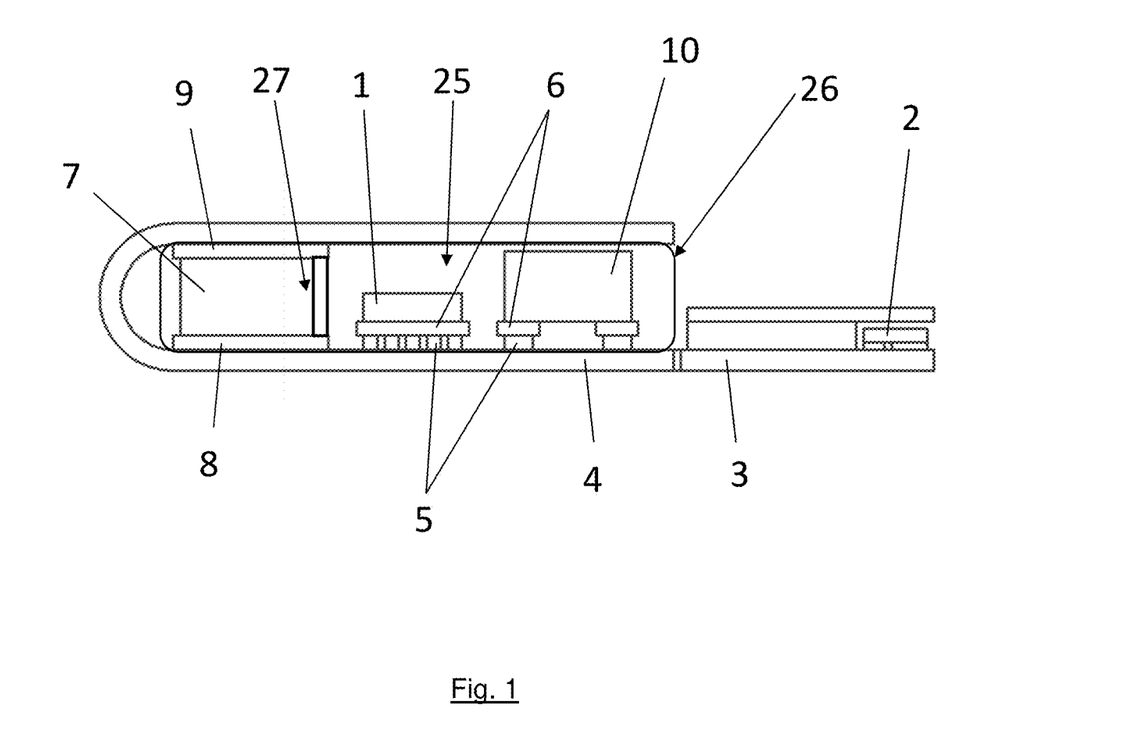
FIG. 1 illustrates the side view of the device.

FIG. 1 shows the device of the invention in side view. The power source 10 and the evaluation electronics 1 in this embodiment are arranged in the direction of the flat support substrate 4 in series.

Figure 2:
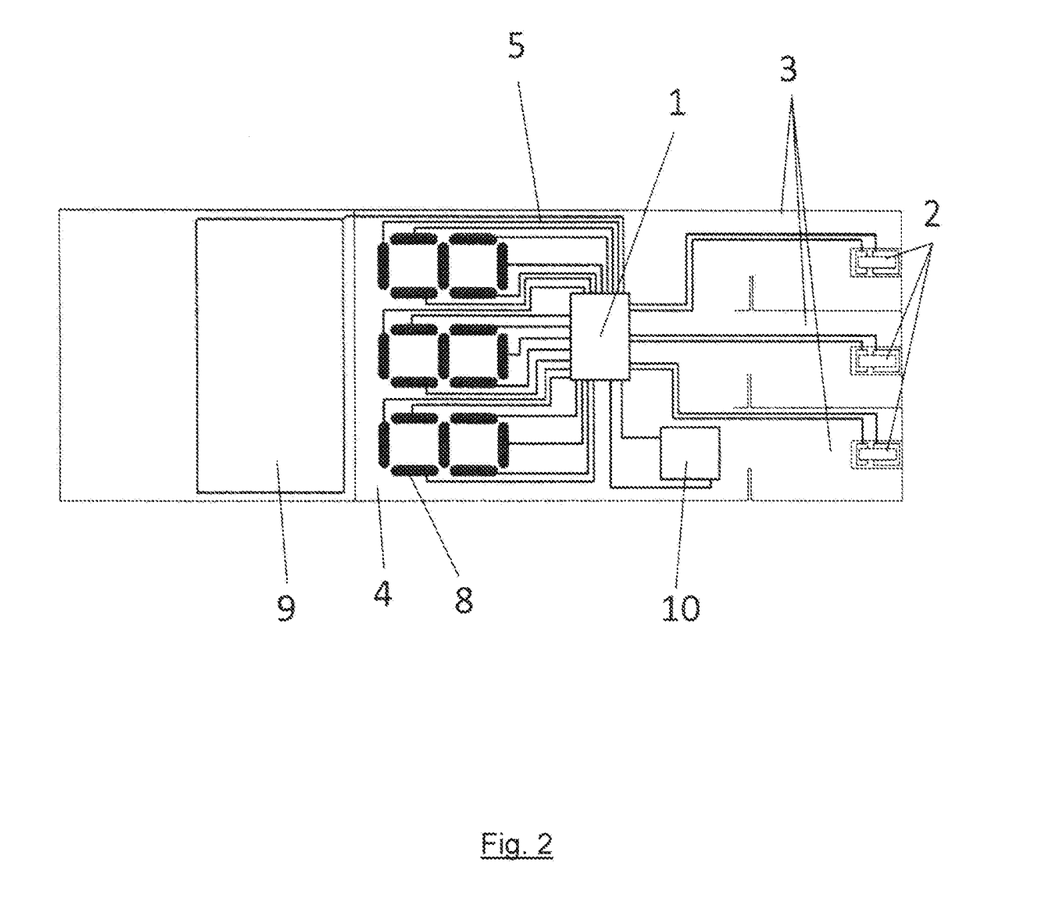
FIG. 2 illustrates the view of the device in unfinished state prior to folding the substrate and prior to placing the top electrode of the display.

FIG. 2 shows a top view of the device from above in an unfinished state prior to folding the support substrate 4 and prior to placing the common electrode 9 of the display 7, wherein the device is composed of a flat support substrate 4, of the electrodes 8 of the display 7 printed by conductive ink, the second transparent common electrode 9 of the display, of the evaluation electronics 1, of the source 10 of energy in the form of batteries, of three disposable test strips 3. In addition, the reduction in the support substrate 4 is shown for mechanical separation of disposable test strips 3. The device is further composed of grounding electrodes of the biosensors 2, of working electrodes of the biosensors 2, of chemistry of the biosensors 2 and of electro-conductive paths forming electrical connections 5 of the individual elements of the device. The support substrate 4 for implementation of the invention is realized by means of glossy polyethylene film (PET) with a thickness of 125 micrometers, corona-charge-treated for improved ink adhesion. Conductive patterns forming electrical connections 5 are realized on this film by means of screen printing technology and electro-conductive silver ink (Creative Materials 125-15). As shown in one example of embodiment, a total of twenty-one separate electrodes 8 of the display 7 is implemented, forming part of the electrochromic display 7, arranged in three groups of seven electrodes 8, where each group represents one digit represented by seven segments, one common electrode 9 of the display 7, three disposable test strips 3 for blood sugar testing and two contacts for connecting the power source 10—batteries. The device of the present invention has several tearable disposable test strips 3 provided with biosensors 2 for blood sugar testing. In an exemplary embodiment, which is preferred, the device has three to eight disposable test strips 3, wherein FIG. 2 shows, for simplicity, only three disposable test strips 3 provided with biosensors 2. However, in the present invention, only two disposable test strips 3 may be arranged or, on the contrary, more than eight, for example twelve, disposable test strips 3. The higher number of disposable test strips 3 is preferable in terms of device price-number of use ratio, the lower number of disposable test strips 3 allows easier handling during use.

The evaluation electronics 1 for use in the device of the invention were developed by means of CMOS technology, specifically 180 nm CMOS technology. The content of the evaluation electronics 1 is primarily the voltage reference 18 and the oscillator 12. The preferred way of implementation of the oscillator 12 is described, for example, in publication "A 51-nW 32.7-kHz CMOS relaxation oscillator with half-period pre-charge compensation scheme for ultra-low power systems", DOI 10.1109/ISCAS.2016.7527369. The oscillator 12 is connected in the system so that it is always powered and provides an output frequency for the other circuits. The voltage reference 18 can be realized as the so-called "band-gap" voltage reference. The particular method of implementation is described in U.S. Pat. No. 7,078,958 B2. The voltage reference 18 should be possible to switch off in order to reduce consumption of integrated circuit, e.g. by means of the switch with the PMOS transistor connected as the so-called "high-side" switch. Another part of the integrated circuit of the evaluation electronics 1 is a temperature sensor 19. Its implementation is described, for example, in Patent Application EP 1 081 477 A1. Like for voltage reference 18, the temperature sensor 19 can be switched off, for example by disconnecting the power supply.

The evaluation electronics 1 of the present invention is encapsulated, in this specific case of embodiment, in the case compatible with surface mounting technology, namely QFN (quad flat no-lead container type).

Figure 3:
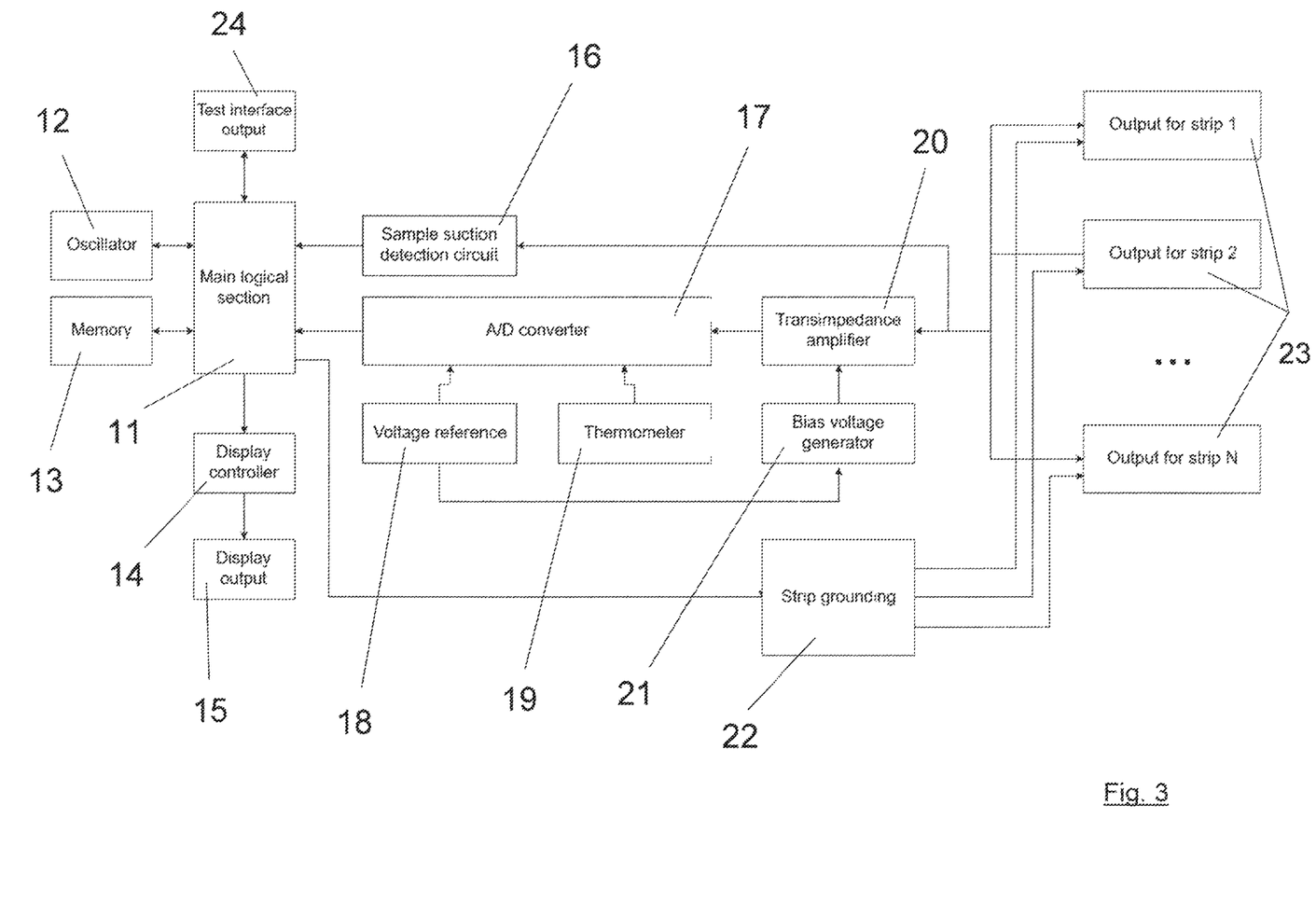
FIG. 3 illustrates the flow diagram of the evaluation electronics.

FIG. 3 shows the flow diagram of the evaluation electronics 1. The evaluation electronics 1 include a main logical section 11 containing a state machine and an interface for communication with other peripherals in an integrated circuit, as well as a single programmable memory device 13 for storing calibration constants in the production, oscillator 12 for generating a clock frequency for logic circuits, test interface output 24 for connecting the instrument to test the device and recording in a single programmable memory device 13, display controller 14, display output 15, voltage reference 18, temperature sensor 19, A/D converter 17, bias voltage generator 21, transimpedance amplifier 20, sample suction detection circuit 16, strip 3 grounding circuit 22 and outputs 23 for strips 3.

Figure 4:
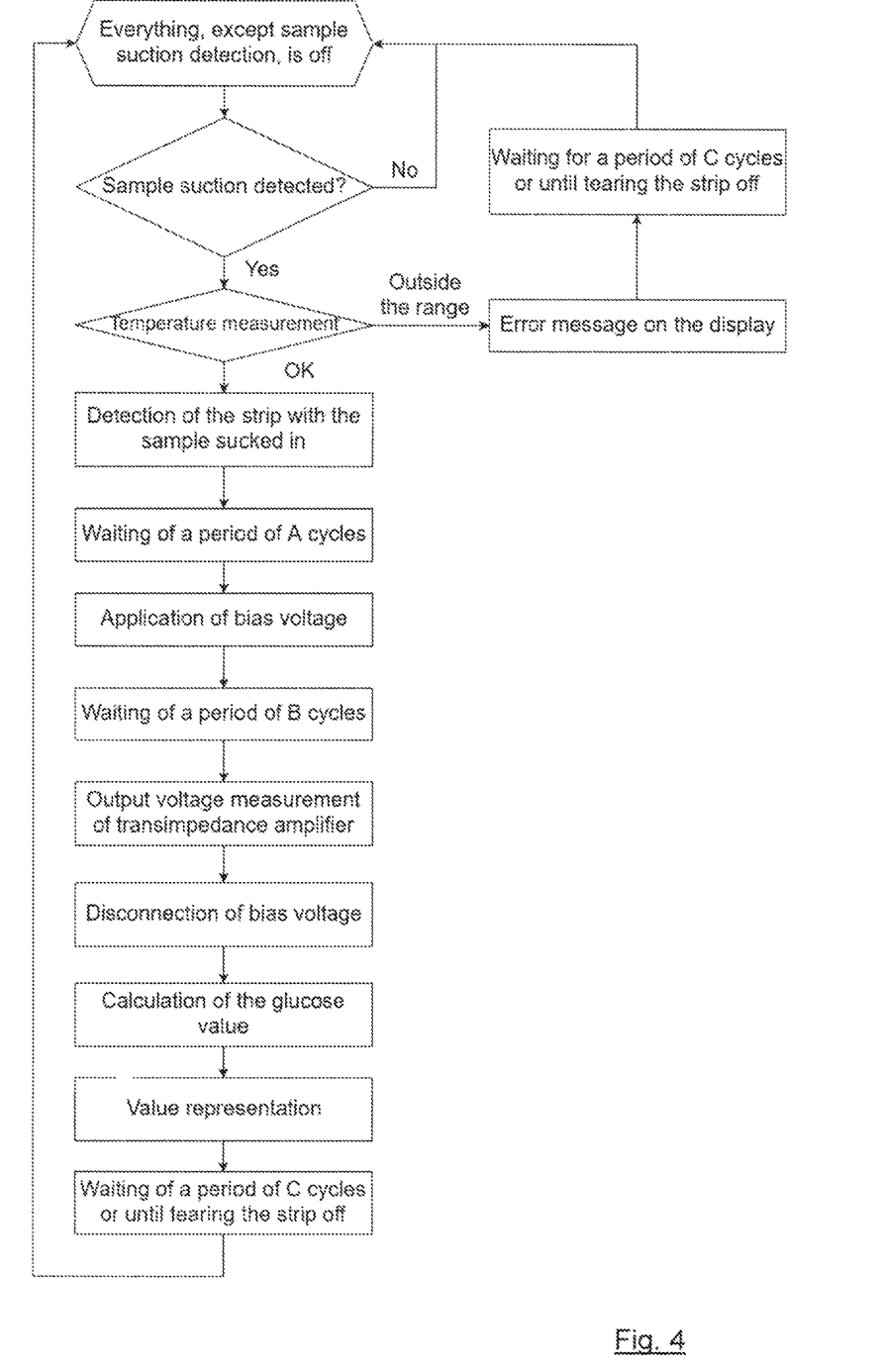
FIG. 4 illustrates the algorithm for evaluation electronics function.

The algorithm for evaluation electronics 1 function, which is shown in FIG. 4, is activated by changing the state of the sample suction detection circuit 16, followed by measurement of the temperature, detection of the strip 3 in which the sample has been sucked, waiting for a period of A cycles, supplying bias voltage to non-inverting input of the transimpedance amplifier 20, waiting for a period of B cycles, measurement of the voltage at the output of the transimpedance amplifier 20, disconnection of the bias voltage, calculation of the glucose value and its displaying for a period of C cycles or until tearing the strip 3. Then, the evaluation electronics 1 change to mode where everything, except sample suction detection, is off. If the temperature measurement is outside the specified range, the display 7 shows an error message and after C cycles or after tearing the strip 3, the evaluation electronics 1 change to the off mode, except for sample suction detection circuit 16.

The display 7 controller 14 is implemented by means of twenty two push-pull drivers, together with control logic. The push-pull driver consists of two transistors implemented on the CMOS technology, one P-MOS and one N-MOS transistor. The gates of the two transistors are interconnected and constitute one input of the push-pull driver. The source P-MOS is connected to the supply voltage, the drain N-MOS of the transistor is interconnected to ground and the remaining two terminals of both transistors are interconnected. They form the output 15 of the display 7 controller 14. Twenty-one of these controllers 14 form the controllers of the individual electrodes 8 of the electrochromic display 7 while the twenty-second circuit is the controller 14 of a common electrode 9 of the display 7. The control logic has a total of twenty-three inputs. Twenty-one inputs are the states of the individual display segments, the twenty-second input connects or disconnects the power supply of the controller 14 of the display 7 and the twenty-third input sets the polarity. Twenty-two outputs of the push-pull circuits lead to the output terminals of the evaluation electronics 1.

In this specific case of embodiment, the sample suction detection circuit 16 is designed in the way that in phase of waiting for sample suction, the grounding electrodes are grounded for disposable test strips 3 by means of strip 3 grounding circuit 22. Pull-up resistors are attached to one of the other electrodes of each strip 3, in this specific case of embodiment, implemented directly on an integrated circuit of the evaluation electronics 1. Applying the blood sample to the strip 3 causes a sudden reduction of electrical resistance, resulting in the drop of voltage on the pull-up resistor.

This reduction in resistance is detected by means of a simple comparator and the device is activated. The next step involves detection of the disposable test strip 3 used. This is achieved by means of disconnection of all earth electrodes of the strips 3 from ground and gradual connection of strip 3 grounding circuit 22. At the moment when the drop is detected, the strip 3, which sucked the blood sample, was identified. This is followed by the test.

The transimpedance amplifier 20 is used to measure the current generated by the disposable test strip 3. This current is proportional to the amount of glucose in the blood sample. N is the number of disposable test strips 3. The non-inverting input of the operational amplifier 20 is connected to the outputs of the working electrodes of disposable test strips 3. The grounding electrode is connected to the strip 3 grounding circuit 22. Positive voltage is connected to the non-inverting input of the operational amplifier 20, in this specific embodiment −300 mV.

This voltage is generated by bias voltage generator 21, in this case of embodiment, implemented by means of the operational amplifier 20 that has the inverting input interconnected to the output and the resistor divider is connected to the non-inverting input, which generates voltage of 300 mV from the voltage of voltage reference. This voltage can be connected or disconnected by means of logic output or the non-inverting input can be connected to 0 V.

The main logical section 11 consists of several separate modules. The first module is the A/D converter 17, in this embodiment of the integrated circuit type SAR (successive approximation register). At the input of the A/D converter 17, there is an analog multiplexer that includes three inputs. An example of the embodiment of the A/D converter 17 is described in U.S. Pat. No. 4,323,887 A. The reference for the A/D converter 17 is the output of voltage reference 18. The output of the A/D converter 17 transforms the voltage value to binary system. The second module is the state machine module. The machine switches between several functional states. The initial functional state is the functional state "sleep". In this functional state, the state machine waits for the change of the logical state of the sample suction detection circuit 16. After the change, it switches to the state "start of test". The first step at the start of the test is the measurement of ambient temperature. The analog multiplexer of the A/D converter 17 switches to the input of the temperature sensor 19 and measures the voltage at the temperature sensor 19. This value will be stored in the memory of the main logical section. If the temperature is outside the permissible range, in this case of embodiment of the invention, less than 0° C. and more than 40° C., the display will show an error message for one minute (constant C) or until tearing strip 3 and the device switches to sleep mode. If the temperature is in the defined range, it switches to the state in which zero voltage is applied to the non-inverting input of the transimpedance amplifier 20 and then it is waited for the number of cycles pre-programmed in a single programmable memory device 13 inside the main logical section 11. In this specific embodiment of the invention, it is waited six seconds, i.e. the number of cycles of the oscillator 12 corresponding to six seconds (constant A). Then, positive voltage is applied to the non-inverting input of the transimpedance amplifier 20 (in this specific case of embodiment: 300 mV) and it is waited for the number of cycles pre-programmed in a single programmable memory device 13 inside the main logical section 11; in this case of embodiment, one and a half seconds (constant B). Then, the A/D converter 17 is used to measure the value of the output of the transimpedance amplifier 20, which is proportional to the concentration of glucose in the sample to be tested. This value is then processed in the ALU of the main logical section 11, in which the glucose value is calculated on the basis of the measured temperature and the measured voltage at the output of the transimpedance amplifier 20. The constants for the calculation of this value are stored in the single programmable memory device 13. In this case of embodiment, the glucose value is then interpreted by means of the BCD decoder in mmol/l units and is drawn by means of the display 7 controller 14 by changing the colours of the individual segments of the electrochromic display 7. After completion of the test, the glucose meter goes to the "sleep mode". The time interval after displaying the value on the display 7 in this specific embodiment of the invention is one minute (constant C) or tearing of the disposable test strip 3, which is electrically detected by change in the comparative level in the sample suction detection circuit 16, whichever of these events occurs first.

The disposable test strips 3, three in this specific case of embodiment, are implemented according to U.S. Pat. No. 5,951,836 A, except that the lower plastic layer is implemented together with the rest of the device so that the test strips 3 form one single unit with the rest of the device. Furthermore, the test strips 3 are provided with a cut-out, which allows the manual tearing of individual test strips 3 from the rest of the device. The next step is the conductive attachment of the evaluation electronics 1 to a flat support substrate 4 by means of an electrically conductive adhesive 6, in this specific case of embodiment using the anisotropically conductive tape ACF7303 (3M). Using the same anisotropically conductive tape, passive components are attached to the substrate, in this case of embodiment, the resistor connected to the pins interconnected to the inverting input or output of the operational amplifier of the potentiostat circuit and two ceramic capacitors with a value of 1 nF and 100 nF connected in parallel to the power supply. The power supply is designed in this specific case of embodiment by means of a primary lithium cell type CR2012, which forms the energy source 10. The conductive connection of the lithium cell of the device is solved by using an isotropically conductive adhesive (Creative Materials 118-15A) for negative and positive battery poles.

The material of the electrochromic display 7 is implemented by means of a mixture of polar solvent and salt which forms an electrolyte and electrochromic active substances. In this specific case of embodiment, the electrolyte is the 50% aqueous zinc chloride solution. Zinc chloride is characterized by being highly hygroscopic. One percent by weight of paraquat is subsequently added to this electrolyte, which is an electrochromic active substance. The electrodes 8 of the display 7—3×7 segments forming three digits are printed on the support substrate 4 using a conductive silver ink. The common electrode 9 placed on the support substrate 4 is also printed using a silver ink. The material of the electrochromic display 7 is placed on the electrodes 8 of the display 7 and the common electrode 9. The unillustrated cover layer is made of a waterproof and water vapour permeable material in foil form, in this case of embodiment: OPSITE FLEXIGRID material. The cover layer is placed on the material of the electrochromic display 7. This completes the construction of the electrochromic display 7 with the function of a desiccant.

Other suitable proved chemical materials for use in the electrolyte of the display 7 are calcium chloride, ferric chloride, potassium carbonate, potassium phosphate, potassium nitrate, potassium hydroxide and sodium hydroxide.

In the design of the display 7 for this device, it was also experimented with other electrochromic materials, specifically polyaniline, which showed a little contrast. Furthermore, the bismuth compounds were tested, which act on the basis of an electro deposition of black particles of bismuth on the surface of the electrodes 8. In such displays 7, the problem with an extreme amount of energy required for complete colouring of the segment is up to 10 times higher than with viologen. Another tested material was ferric ferrocyanide, which achieved a good contrast. Use of viologen for the design of the device of the present invention is the best. Use of ferric ferrocyanide is also preferred.

The device is tested using the test device and test sequence, the purpose of which in this case of the test is the continuity of electrical connections 5, testing the voltage of voltage reference 18, testing the function of the A/D converter 17, measuring the frequency of the oscillator 12, entering the values in a single programmable memory device 13 and completing the test.

Continuity testing of the paths is solved by applying a matrix of test points to the support substrate 4 with printed electrical connections 5 and fitted with the evaluation electronics 1 with the other passive components. Via the communication interface, the evaluation electronics 1 are instructed to gradually apply positive supply voltage to each input and output separately. The test device checks if all conductive paths are continuous and if there is no short-circuit between any two conductive paths. After successful completion of this test, the functionality of the A/D converter 17 and the voltage reference 18 is tested. The so-called "bias" voltage is applied to the working electrodes of disposable test strips 3, which is measured by a test device, simultaneously measuring the value of this "bias" voltage by the A/D converter 17 and compared with the expected value. If the measured result is compliant, in this case of embodiment, with a tolerance of less than 1% compared to the actual value, the next part of the test takes place, which is the measurement of the frequency of the oscillator 12. One of the output terminals of the integrated circuit of the evaluation electronics 1 indicates a rectangular signal, in this case of embodiment consistent with the frequency of the oscillator 12, this frequency is measured and based on it, constants are determined and in the next step entered in a single programmable memory device 13 of the evaluation electronics 1. In this case of embodiment, these constants are the serial number of the device, which is different for each produced device, as well as the constant A, which in this case corresponds to the oscillator frequency in Hz multiplied by six seconds, the constant B, which corresponds to the oscillator frequency in Hz multiplied by one and a half seconds, and the constant C, which corresponds to the oscillator frequency in Hz multiplied by sixty seconds. After entering the calibration constants and termination of all previous phases of the test, the testing of the device is completed. In case of failure of any of the above tests, the device is sorted out.

INDUSTRIAL APPLICABILITY

A device for random blood sugar testing and the method of its use of the invention can be applied in health care sector.

LIST OF REFERENCE NUMERALS 1) evaluation electronics
2) biosensor
3) disposable test strip
4) support substrate
5) electrical connections
6) electrically conductive adhesive
7) electrochromic display
8) display electrode
9) common display electrode
10) energy source
11) main logical section
12) oscillator
13) memory device
14) display controller
15) display output
16) sample suction detection circuit
17) A/D converter
18) voltage reference
19) temperature sensor
20) transimpedance amplifier
21) bias voltage generator
22) strip grounding circuit
23) output for strip
24) test interface output
25) common vapour non-permeable closable space
26) removable and/or openable vapour non-permeable package
27) vapour permeable cover barrier layer

The invention claimed is:

1. A device for random blood sugar testing comprising of at least one disposable biosensor (2) for applying a blood sample, as well as evaluation electronics (1) for retrieving and processing information from the at least one disposable biosensor (2) with the applied blood sample, as well as a display (7) for displaying information from the evaluation electronics (1), wherein the at least one disposable biosensor (2) and the display (7) are arranged in a common vapour non-permeable closable space, wherein the display (7) is hygroscopic, and the display (7) is electrochromic, wherein an electrolyte of the electrochromic display has desiccant properties.

2. The device according to claim 1, wherein the display (7), evaluation electronics (1) and the at least one disposable biosensor (2) are arranged on a common support substrate (4), wherein the support substrate (4) is provided with the common vapour non-permeable closable space, the common vapour non-permeable closable space being within a removable and/or openable vapour non-permeable package.

3. The device according to claim 2, wherein the at least one disposable biosensor (2) is separable from the support substrate (4).

4. The device according to claim 1, wherein the electrolyte of the electrochromic display (7) contains at least one chemical substance of the group of zinc chloride, calcium chloride, ferric chloride, potassium carbonate, potassium phosphate, potassium nitrate, potassium hydroxide, and sodium hydroxide.

5. The device according to claim 1, wherein the electrochromic display (7) contains at least one electrochromic substance of the group of viologen, complex iron compound, PEDOT:PSS, polyaniline, and polypyrrole.

6. The device according to claim 1, wherein the display (7) is provided with a vapour permeable cover barrier layer for water-based liquids.

7. The device according to claim 1, wherein the at least one disposable biosensor (2) is provided with at least one enzyme of the group of glucose oxidase, glucose dehydrogenase, and peroxidase.

8. The device according to claim 1, wherein the evaluation electronics (1) comprises at least one memory device (13)

with stored calibration constants of disposable biosensors (2) and/or oscillator frequency.

\* \* \* \* \*